US012765573B2

(12) United States Patent
Wu et al.

(10) Patent No.: US 12,765,573 B2
(45) Date of Patent: Oct. 20, 2026

(54) SOFT CANDY WITHOUT FISHY TASTE OR ODOR AND PREPARATION METHOD THEREOF

(71) Applicant: JIANGSU YICHAO HEALTH TECHNOLOGY CO., LTD., Huaian (CN)

(72) Inventors: Kaihong Wu, Huaian (CN); Weijia Li, Huaian (CN); Bingchai Lin, Huaian (CN); Hongyi Lin, Huaian (CN); Xiaoqing Yang, Huaian (CN)

(73) Assignee: JIANGSU YICHAO HEALTH TECHNOLOGY CO., LTD., Huaian (CN)

( * ) Notice: Subject to any disclaimer, the term of this patent is extended or adjusted under 35 U.S.C. 154(b) by 260 days.

(21) Appl. No.: 18/387,442

(22) Filed: Nov. 6, 2023

(65) Prior Publication Data

US 2024/0188582 A1 Jun. 13, 2024

Related U.S. Application Data

(63) Continuation of application No. PCT/CN2022/140188, filed on Dec. 20, 2022.

(30) Foreign Application Priority Data

Dec. 12, 2022 (CN) ......................... 202211589691.4

(51) Int. Cl.

| | |
|---|---|
| ***A23G 3/40*** | (2006.01) |
| ***A23G 3/34*** | (2006.01) |
| ***A23G 3/36*** | (2006.01) |
| ***A23G 3/42*** | (2006.01) |
| ***A23G 3/48*** | (2006.01) |
| ***A61K 9/00*** | (2006.01) |
| ***A61K 31/202*** | (2006.01) |
| ***A61K 31/355*** | (2006.01) |
| ***A61K 36/537*** | (2006.01) |

(52) U.S. Cl.

CPC ............. *A23G 3/40* (2013.01); *A23G 3/0027* (2013.01); *A23G 3/368* (2013.01); *A23G 3/42* (2013.01); *A23G 3/48* (2013.01); *A61K 9/0056* (2013.01); *A61K 31/202* (2013.01); *A61K 31/355* (2013.01); *A61K 36/537* (2013.01)

(58) Field of Classification Search

CPC ...... A61K 31/202; A61K 9/0056; A23G 3/42; A23G 3/0027

See application file for complete search history.

(56) References Cited

U.S. PATENT DOCUMENTS

2018/0344633 A1* 12/2018 Sato ..................... A61K 9/0056

FOREIGN PATENT DOCUMENTS

CN 102422960 A * 4/2012
CN 103416759 A * 12/2013

OTHER PUBLICATIONS

CN-102422960-A (Google English translation, downloaded Mar. 2026) (Year: 2026).*
CN-103416759-A (Google English translation, downloaded Mar. 2026) (Year: 2026).*

* cited by examiner

*Primary Examiner* — Mark V Stevens

(57) ABSTRACT

Disclosed are a soft candy without a fishy taste or odor and a preparation method thereof. The preparation method includes: (1) mixing and stirring a DHA-containing raw oil, a fragrance, and an antioxidant, and allowing a resulting mixture to stand to obtain a DHA-containing mixture; (2) mixing and dispersing a polymeric sugar, an emulsifying agent, and water to obtain an oxygen-isolation preprepared solution; (3) dispersing the oxygen-isolation preprepared solution and the DHA-containing mixture, and allowing a resulting system to undergo equilibrium and stabilization to obtain an oxygen-isolated DHA-containing solution; (4) preparation of a pigment solution and an acid solution; (5) preparation of a sticky syrup; (6) mixing the sticky syrup, the oxygen-isolated DHA-containing solution, the acid solution, and the pigment solution to obtain a sugar-containing slurry; and (7) pouring the sugar-containing slurry into a soft candy mold to obtain the soft candy without a fishy taste or odor.

10 Claims, No Drawings

SOFT CANDY WITHOUT FISHY TASTE OR ODOR AND PREPARATION METHOD THEREOF

CROSS-REFERENCE TO RELATED APPLICATIONS

The present application is a continuation application of PCT application No. PCT/CN2022/140188 filed on Dec. 20, 2022, which claims the benefit of Chinese Patent Application No. 202211589691.4 filed on Dec. 12, 2022. The contents of all of the aforementioned applications are incorporated by reference herein in their entirety.

TECHNICAL FIELD

The present disclosure belongs to the field of food processing, and specifically relates to a soft candy without a fishy taste or odor and a preparation method thereof.

BACKGROUND

Fish oil is mainly derived from marine fish and is a general term for all fats in fish, including body oil, glycerin, and brain oil. Fish oil is obtained by steaming and pressing fish and wastes in the fish and separating a product. Algal oil is a pure plant-based docosahexaenoic acid (DHA). Fish oil and algal oil each includes three major components, namely Omega-3 fatty acids, DHAs, and eicosapentaenoic acids (EPA). Fish oil and algal oil not only have antibacterial, anti-inflammatory, and blood lipid-regulating effects, but also have an effect of preventing cardiovascular diseases (CVDs). DHA, commonly known as brain gold, is a polyunsaturated fatty acid (PUFA) very important for the human body and is an important member of the Omega-3 unsaturated fatty acid (UFA) family. DHA is a major element for cell growth and maintenance of a nervous system and an important constitutive fatty acid for a brain and retina. A content of DHA in a human cerebral cortex is as high as 20%, and a content of DHA in a retina of eyes is about 50%, which is the highest. Studies have shown that DHA is very closely related to brain health. Increasing a content of DHA in a food can improve a DHA level in a brain, thereby facilitating the enhancement of learning and memory functions, the healthy development of a brain and nerves, and the prevention and treatment of impaired vision and Alzheimer's disease (AD). In addition, DHA has anti-aging, blood circulation-improving, and blood lipid-lowering effects.

Fish oil and algal oil are rich in UFAs, which are easy to undergo oxidative rancidity and are sensitive to heat, water, and oxygen. Therefore, preservation and processing manners for fish oil and algal oil are relatively limited, and generally, supplements of fish oil and algal oil are in a form of an oil, such as a drop and a soft capsule. A DHA supplement in a form of an oil often leads to unpleasant tasting experience, a drop thereof will cause esophageal discomfort and bad breath, and a soft capsule thereof often cause difficult swallowing due to a too-large size. There are a small number of fish oil supplements in forms of soft candies on the market. However, due to a high processing temperature and a high moisture content in the soft candy products, fish oil in these soft candy products will be oxidized very fast, which makes these fish oil products have problems such as obvious fishy taste or odor, or low addition level.

SUMMARY

A technical problem to be solved by the present disclosure is to provide a soft candy without a fishy taste or odor and a preparation method thereof. In the present disclosure, a preparation process of a soft candy is improved, such that the soft candy finally prepared not only has a high content of DHA-containing raw oil, but also exhibits high stability and prominent taste.

In order to achieve the above objective, the present disclosure adopts the following technical solutions: A preparation method of a soft candy without a fishy taste or odor is provided, including the following steps:

(1) preparation of a DHA-containing mixture, including mixing and stirring a DHA-containing raw oil, a fragrance, and an antioxidant, and allowing a resulting mixture to stand to obtain the DHA-containing mixture;

(2) preparation of an oxygen-isolation preprepared solution, including mixing a polymeric sugar, an emulsifying agent, and water, and subjecting a resulting mixture to dispersion with a shearing device to obtain the oxygen-isolation preprepared solution;

(3) preparation of an oxygen-isolated DHA-containing solution, including adding the oxygen-isolation preprepared solution and the DHA-containing mixture to a dispersion device to allow dispersion, and allowing a resulting system to undergo equilibrium and stabilization to obtain the oxygen-isolated DHA-containing solution;

(4) preparation of a pigment solution and an acid solution;

(5) preparation of a sticky syrup;

(6) preparation of a slurry, including mixing the sticky syrup, the oxygen-isolated DHA-containing solution, the acid solution, and the pigment solution to obtain a sugar-containing slurry; and (7) pouring, including pouring the sugar-containing slurry into a soft candy mold for shaping to obtain the soft candy without the fishy taste or odor.

In the preparation method of a soft candy without a fishy taste or odor in the present disclosure, the polymeric sugar and emulsifying agent are subjected to dispersion with a high-accuracy shearing device at a specified rotational speed, such that molecules are evenly distributed in a space at a specified stable spacing to obtain an oxygen-isolation preprepared solution with a honeycomb spatial structure; the oxygen-isolation preprepared solution is placed in an oxygen-isolation container with a high-efficiency dispersion device, nitrogen pumping is started, the DHA-containing raw oil is added, and the high-efficiency dispersion device is turned on to allow dispersion for an appropriate time, such that micro-scale fine oil droplets are produced from the DHA-containing raw oil and dispersed in the honeycomb structure to obtain a DHA-containing raw oil dispersion; and the DHA-containing raw oil dispersion is equilibrated and stabilized for an appropriate time, such that the polymeric sugar honeycomb structure constructed through hydrogen bonding gradually forms an internal hydrophobic circle under an action of non-polar groups of internal DHA-containing raw oil particles, and thus the DHA-containing raw oil particles are tightly wrapped to obtain an oxygen-isolated DHA-containing raw oil solution, which allows a strong oxygen-isolation effect. In the present disclosure, the oxygen-isolation treatment for the DHA-containing raw oil can make the DHA-containing raw oil maintain excellent stability under subsequent processing conditions, and prevent DHA from rancidity and oxidative deterioration caused by factors such as heat, oxygen, and moisture.

As a preferred embodiment of the preparation method of a soft candy without a fishy taste or odor in the present disclosure, in step (1), the mixing and stirring is conducted at 10° C. to 35° C.

As a preferred embodiment of the preparation method of a soft candy without a fishy taste or odor in the present disclosure, in step (2), the dispersion is conducted at 30° C. to 90° C., and a rotational speed of the shearing device is 1,000 rpm to 6,000 rpm. More preferably, in step (2), the dispersion is conducted at 40° C. to 70° C., and a rotational speed of the shearing device is 2,000 rpm to 4,000 rpm; and under these preferred conditions, the prepared oxygen-isolation preprepared solution has a uniform molecular distribution.

As a preferred embodiment of the preparation method of a soft candy without a fishy taste or odor in the present disclosure, in step (3), the dispersion is conducted for 10 min to 60 min, and the equilibrium and stabilization is conducted for 0.5 h to 3 h. More preferably, in step (3), the dispersion is conducted for 20 min to 30 min, and the equilibrium and stabilization is conducted for 1 h to 1.5 h; and under these preferred conditions, fish oil particles in the prepared oxygen-isolated fish oil-containing solution are more tightly wrapped and have better stability.

As a preferred embodiment of the preparation method of a soft candy without a fishy taste or odor in the present disclosure, when the mixing in step (6) is conducted at 50° C. to 75° C. the mixing is conducted for less than 30 min; and when the mixing in step (6) is conducted at 76° C. to 100° C., the mixing is conducted for less than 20 min. More preferably, when the mixing in step (6) is conducted at 50° C. to 75° C., the mixing is conducted for less than 15 min; and when the mixing in step (6) is conducted at 76° C. to 100° C., the mixing is conducted for less than 10 min.

As a preferred embodiment of the preparation method of a soft candy without a fishy taste or odor in the present disclosure, when the sugar-containing slurry in step (7) has a temperature of 50° C. to 75° C., the pouring for shaping is conducted for less than 2 h; and when the sugar-containing slurry in step (7) has a temperature of 76° C. to 100° C., the pouring for shaping is conducted for less than 1 h.

As a preferred embodiment of the preparation method of a soft candy without a fishy taste or odor in the present disclosure, based on a mass of the DHA-containing raw oil, a mass percentage of the polymeric sugar is 30% to 80%, a mass percentage of the emulsifying agent is 0.1% to 30%, a mass percentage of the fragrance is 0.1% to 50%, and a mass percentage of the antioxidant is 0.1% to 5%. More preferably, a mass percentage of the polymeric sugar is 50% to 70%, a mass percentage of the emulsifying agent is 2% to 20%, a mass percentage of the fragrance is 2% to 10%, and a mass percentage of the antioxidant is 0.4% to 2%. In the present disclosure, by screening types and contents of each component in the soft candy, the prepared soft candy exhibits high stability and excellent flavor while having a high content of functional component.

As a preferred embodiment of the preparation method of a soft candy without a fishy taste or odor in the present disclosure, the preparation method involves at least one selected from the group consisting of the following (a) to (f):

(a) the fragrance is selected from the group consisting of a citrus fragrance, a berry fragrance, and a mixture thereof, but is not limited thereto;

(b) the antioxidant is selected from the group consisting of a rosemary extract, vitamin E, vitamin C, a tea polyphenol, a phospholipid, and a mixture thereof, but is not limited thereto;

(c) the polymeric sugar is selected from the group consisting of gum arabic, fructo-oligosaccharide (FOS), α-cyclodextrin, β-cyclodextrin, γ-cyclodextrin, maltodextrin, polydextrose, inulin, pectin, carrageenan, guar gum, starch acetate, acetylated distarch, and a mixture thereof, but is not limited thereto;

(d) the emulsifying agent is selected from the group consisting of mono- and diglycerides of fatty acid, sucrose fatty acid esters, phospholipids, citric and fatty acid esters of glycerol (CITREM), acetylated mono- and diglycerides of fatty acid, sodium caseinate, lactic and fatty acid esters of glycerol (LACTEM), and a mixture thereof, but is not limited thereto;

(e) a sugar used in preparation of the sticky syrup is selected from the group consisting of maltitol, isomaltitol, glucose, white granulated sugar, and a mixture thereof, but is not limited thereto; and (f) the DHA-containing raw oil is selected from the group consisting of fish oil, algal oil, and a mixture thereof, but is not limited thereto.

As a preferred embodiment of the preparation method of a soft candy without a fishy taste or odor in the present disclosure, the soft candy without a fishy taste or odor includes at least one selected from the group consisting of an animal glue-based soft candy, a plant gum-based soft candy, a mixed glue-based soft candy, a filled soft candy, a coated soft candy, and a double-layer soft candy.

In the present disclosure, flavor spectrum analysis is conducted with an electronic nose to screen out a fragrance that matches a fishy odor, and the fragrance is preferably a fruit fragrance, where citrus and berry fragrances are the most preferred.

The present disclosure has the following beneficial effects: The present disclosure provides a soft candy without a fishy taste or odor and a preparation method thereof. In the present disclosure, a soft candy is adopted as a carrier, and fish oil is masked and pre-isolated from oxygen to greatly reduce an oxidation rate of fish oil in the soft candy and improve the stability. In addition, the prepared soft candy has a high fish oil content and an excellent flavor without a fishy taste or odor, which solves the problem that the existing fish oil-containing soft candy causes unpleasant intake experience due to a fishy taste or odor when serving as a dietary supplement, and has a low fish oil content. In the present disclosure, on the basis of the masking and pre-oxygen isolation treatments of fish oil, process conditions of a production process are strictly controlled to reduce the influence of factors such as heat, oxygen, and moisture on the stability and flavor of the fish oil-containing soft candy.

DETAILED DESCRIPTION

In order to concisely and clearly demonstrate the technical solutions, objectives, and advantages of the present disclosure, the technical solutions of the present disclosure are described in detail below in conjunction with specific examples. Unless otherwise specified, the reagents involved in the examples of the present disclosure are commercially-available products and can be purchased through commercial channels.

Example 1

In this example, a soft candy without a fishy taste or odor was provided, including the following components in parts by weight: maltitol solution: 60 parts; isomaltitol: 20 parts; pectin: 2 parts; sodium citrate: 0.5 part; fish oil: 10 parts;

orange fragrance: 0.4 part; lemon fragrance: 0.2 part; rosemary extract: 0.1 part; vitamin E oil: 0.1 part; gum arabic: 2 parts; α-cyclodextrin: 0.5 part; starch acetate: 2.5 parts; sucrose fatty acid ester: 0.5 part; ß-carotene powder: 0.1 part; and citric acid: 1.2 parts.

A preparation method of the soft candy without a fishy taste or odor in this example included the following steps:

(1) Preparation of a fish oil-containing mixture: 10 parts of the fish oil, 0.4 part of the orange fragrance, 0.2 part of the lemon fragrance, 0.1 part of the rosemary extract, and 0.1 part of the vitamin E oil were mixed and stirred at 25° C., and then allowed to stand for 45 min to obtain the fish oil-containing mixture.

(2) Preparation of an oxygen-isolation preprepared solution: 2 parts of the gum arabic, 0.5 part of the α-cyclodextrin, 2.5 parts of the starch acetate, and 0.5 part of the sucrose fatty acid ester were thoroughly mixed, 5 parts of 60° C. purified water were added, and a resulting mixture was subjected to high-speed shearing at 3,500 rpm to obtain the oxygen-isolation preprepared solution.

(3) Preparation of an oxygen-isolated fish oil-containing solution: The oxygen-isolation preprepared solution was added to the fish oil-containing mixture, and a resulting mixture was subjected to efficient dispersion for 20 min and then equilibrated for 1 h to obtain the oxygen-isolated fish oil-containing solution.

(4) Preparation of a pigment solution and an acid solution: 0.1 part of the ß-carotene powder was added to 0.2 part of the purified water, and a resulting mixture was stirred for thorough dissolution to obtain the pigment solution; and 1.2 parts of the citric acid were added to 2.4 parts of the purified water, and a resulting mixture was stirred for thorough dissolution to obtain the acid solution.

(5) Preparation of a sticky syrup: 2 parts of the pectin, 0.5 part of the sodium citrate, and 5 parts of the isomaltitol were thoroughly mixed, then 20 parts of the purified water were added, and a resulting mixture was thoroughly stirred at a high speed and then decocted until the mixture was slightly boiled; and then 15 parts of the isomaltitol and 60 parts of the maltitol solution were added and dissolved, and a resulting system was further decocted until a solid content was 80% to obtain the sticky syrup, which was stored at 90° C. for later use.

(6) Preparation of a slurry: The sticky syrup, the oxygen-isolated fish oil-containing solution, the acid solution, and the pigment solution were mixed to obtain a sugar-containing slurry. This step was completed within 8 min to 10 min.

(7) Pouring: The sugar-containing slurry was poured into a soft candy mold for shaping to obtain a soft candy without a fishy taste or odor. This step was completed within 10 min.

(8) Drying: The soft candy without a fishy taste or odor obtained after the shaping was dried until a moisture content was 15% to 18%.

(9) Demolding and varnishing: The dried soft candy was demolded and varnished to obtain a fish oil-containing pectin soft candy without a fishy taste or odor.

Example 2

In this example, a soft candy without a fishy taste or odor was provided, including the following components in parts by weight: glucose syrup: 30 parts; white granulated sugar: 30 parts; gelatin: 7.2 parts; sodium citrate: 0.1 part; algal oil: 25 parts; strawberry fragrance: 0.6 part; blackcurrant fragrance: 0.3 part; phospholipid: 0.1 part; vitamin E oil: 0.2 part; polydextrose: 5 parts; γ-cyclodextrin: 2.5 parts; maltodextrin: 5 parts; mono- and diglycerides of fatty acid: 0.8 part; purple carrot juice: 0.1 part; and citric acid: 1.5 parts.

A preparation method of the soft candy without a fishy taste or odor in this example included the following steps:

(1) Preparation of an algal oil-containing mixture: 25 parts of the algal oil, 0.6 part of the strawberry fragrance, 0.3 part of the blackcurrant fragrance, 0.1 part of the phospholipid, and 0.2 part of the vitamin E oil were mixed and stirred at 25° C., and then allowed to stand for 45 min to obtain the algal oil-containing mixture.

(2) Preparation of an oxygen-isolation preprepared solution: 5 parts of the polydextrose, 2.5 parts of the γ-cyclodextrin, 5 parts of the maltodextrin, and 0.8 part of the mono- and diglycerides of fatty acid were thoroughly mixed, 8 parts of 60° C. purified water were added, and a resulting mixture was subjected to high-speed shearing at 4,000 rpm to obtain the oxygen-isolation preprepared solution.

(3) Preparation of an oxygen-isolated algal oil-containing solution: The oxygen-isolation preprepared solution was added to the algal oil-containing mixture, and a resulting mixture was subjected to efficient dispersion for 25 min and then equilibrated for 1 h to obtain the oxygen-isolated algal oil-containing solution.

(4) Preparation of an acid solution: 1.5 parts of the citric acid were added to 3 parts of the purified water, and a resulting mixture was stirred for thorough dissolution to obtain the acid solution.

(5) Preparation of a sticky syrup: 7.2 parts of the gelatin were added to 10 parts of 80° C. to 90° C. purified water, and a resulting mixture was stirred for 30 min to allow thorough dissolution to obtain a gelatin solution; 30 parts of the glucose syrup, 30 parts of the white granulated sugar, and 0.1 part of the sodium citrate were added to a decocting pot, 5 parts of purified water were added, and a resulting mixture was heated for dissolution and decocted until a solid content was 84% to obtain a syrup; and the gelatin solution was mixed with the syrup to obtain the sticky syrup.

(6) Preparation of a slurry: The sticky syrup, the oxygen-isolated algal oil-containing solution, the acid solution, and 0.1 part of the purple carrot juice were mixed and stirred to obtain a sugar-containing slurry. This step was completed within 10 min to 12 min.

(7) Pouring: The sugar-containing slurry was poured into a soft candy mold for shaping. This step was completed within 20 min.

(8) Drying: A soft candy without a fishy taste or odor obtained after the shaping was dried until a moisture content was 15% to 18%.

(9) Demolding and varnishing: The dried soft candy was demolded and varnished to obtain an algal oil-containing pectin soft candy without a fishy taste or odor.

Example 3

In this example, a fish oil-containing filled soft candy with a compounded flavor and without a fishy taste or odor was provided, including the following components in parts by weight:

Core: glucose syrup: 40 parts; white granulated sugar: 30 parts; pectin: 2 parts; sodium citrate: 0.4 part; fish oil: 20 parts; mango fragrance: 0.8 part; rosemary extract: 0.2 part; vitamin E oil: 0.1 part; polydextrose: 6 parts; α-cyclodextrin: 1 part; starch acetate: 5 parts; sucrose fatty acid ester: 0.6 part; β-carotene powder: 0.4 part; and citric acid: 1.2 parts. Skin: glucose syrup: 55 parts; white granulated sugar: 35 parts; gelatin: 8 parts; sodium citrate: 0.1 part; passionflower fragrance: 0.4 part; and citric acid: 1.5 parts.

A preparation method of the filled soft candy without a fishy taste or odor in this example included the following steps:

(1) Preparation of a fish oil-containing mixture (core material): 20 parts of the fish oil, 0.8 part of the mango fragrance, 0.2 part of the rosemary extract, and 0.1 part of the vitamin E oil were mixed and stirred at 25° C., and a resulting mixture was allowed to stand for 45 min to obtain the fish oil-containing mixture A.

(2) Preparation of an oxygen-isolation preprepared solution (core material): 6 parts of the polydextrose, 1 part of the α-cyclodextrin, 5 parts of the starch acetate, and 0.6 part of the sucrose fatty acid ester were thoroughly mixed, 10 parts of 60° C. purified water were added, and a resulting mixture was subjected to high-speed shearing at 4,000 rpm to obtain the oxygen-isolation preprepared solution B.

(3) Preparation of an oxygen-isolated fish oil-containing solution (core material): The oxygen-isolation preprepared solution B was added to the fish oil-containing mixture A, and a resulting mixture was subjected to efficient dispersion for 30 min and then equilibrated for 1 h to obtain the oxygen-isolated fish oil-containing solution C.

(4) Preparation of a pigment solution (core material): 0.4 part of the β-carotene powder was added to 0.8 part of the purified water, and a resulting mixture was stirred for thorough dissolution to obtain the pigment solution D.

(5) Preparation of an acid solution (core material): 1.2 parts of the citric acid were added to 2.4 parts of the purified water, and a resulting mixture was stirred for thorough dissolution to obtain the acid solution E.

(6) Preparation of an acid solution (skin material): 1.5 parts of the citric acid were added to 3 parts of the purified water, and a resulting mixture was stirred for thorough dissolution to obtain the acid solution F.

(7) Preparation of a pectin solution (core material): 2 parts of the pectin, 0.4 parts of the sodium citrate, and 5 parts of the white granulated sugar were thoroughly mixed, then 20 parts of the purified water were added, and a resulting mixture was thoroughly stirred at a high speed to obtain the pectin solution G.

(8) Preparation of a gelatin solution (skin material): 8 parts of the gelatin were added to 12 parts of 80° C. to 90° C. purified water, and a resulting mixture was stirred for 30 min to allow thorough dissolution to obtain the gelatin solution H.

(9) Decocting of core materials: The pectin solution G was added to a decocting pot and decocted until the pectin solution was slightly boiled, then the remaining 25 parts of white granulated sugar and 40 parts of glucose syrup were added, and a resulting mixture was heated for dissolution and further decocted until a solid content was 80% to obtain a sticky syrup for the core, which was stored at 90° C. for later use.

(10) Preparation of a core material slurry: The oxygen-isolated fish oil-containing solution C, the pigment solution D, and the acid solution E were added to the sticky syrup for the core obtained in step 9, and a resulting mixture was stirred to obtain the core material slurry. This step was completed within 8 min to 10 min.

(11) Decocting of skin materials: 35 parts of the white granulated sugar, 55 parts of the glucose syrup, and 0.1 part of the sodium citrate were added to a decocting pot, 5 parts of the purified water were added, and a resulting mixture was heated for dissolution and decocted until a solid content was 84% to obtain a syrup for later use.

(12) Preparation of a sticky syrup for the skin: The gelatin solution H was added to the syrup obtained in step 11, and a resulting mixture was thoroughly mixed to obtain the sticky syrup for the skin.

(13) Preparation of a skin material slurry: 0.4 part of the passionflower fragrance and the acid solution F were added to the sticky syrup for the skin obtained in step 12, and a resulting mixture was stirred to obtain the skin material slurry.

(14) Pouring: The core material slurry obtained in step 10 and the skin material slurry obtained in step 13 were poured into a soft candy mold in a weight ratio of 1:1 for shaping, during which the core material slurry was kept in the center and was completely wrapped by the skin material slurry. This step was completed within 10 min.

(15) Drying: A soft candy obtained after the shaping was dried in a drying room until a moisture content was 15% to 18%.

(16) Demolding and varnishing: The dried soft candy was demolded and varnished to obtain the fish oil-containing filled soft candy without a fishy taste or odor.

Comparative Example 1

This comparative example was different from Example 1 in that the soft candy without a fishy taste or odor in this comparative example had a different formula. The soft candy without a fishy taste or odor in this comparative example included the following components in parts by weight: maltitol solution: 60 parts; isomaltitol: 20 parts; pectin: 2 parts; sodium citrate: 0.5 part; fish oil: 10 parts; rosemary extract: 0.7 part; vitamin E oil: 0.1 part; gum arabic: 2 parts; α-cyclodextrin: 0.5 part; starch acetate: 2.5 parts; sucrose fatty acid ester: 0.5 part; β-carotene powder: 0.1 part; and citric acid: 1.2 parts.

Comparative Example 2

This comparative example was different from Example 1 in that the soft candy without a fishy taste or odor in this comparative example had a different formula. The soft candy without a fishy taste or odor in this comparative example included the following components in parts by weight: maltitol solution: 60 parts; isomaltitol: 20 parts; pectin: 2 parts; sodium citrate: 0.5 part; fish oil: 10 parts; orange fragrance: 0.4 part; lemon fragrance: 0.2 part; gum arabic: 2 parts; α-cyclodextrin: 0.5 part; starch acetate: 2.5 parts; sucrose fatty acid ester: 0.5 part; β-carotene powder: 0.1 part; and citric acid: 1.2 parts.

Comparative Example 3

This comparative example was different from Example 1 in that the soft candy without a fishy taste or odor in this comparative example had a different formula. The soft candy without a fishy taste or odor in this comparative example included the following components in parts by weight: maltitol solution: 60 parts; isomaltitol: 20 parts; pectin: 2 parts; sodium citrate: 0.5 part; fish oil: 10 parts;

orange fragrance: 0.4 part; lemon fragrance: 0.2 part; rosemary extract: 0.1 part; vitamin E oil: 0.1 part; maltitol powder: 5 parts; sucrose fatty acid ester: 0.5 part; β-carotene powder: 0.1 part; and citric acid: 1.2 parts.

Comparative Example 4

This comparative example was different from Example 1 in that step (3) of the preparation method of the soft candy in this comparative example was as follows: the oxygen-isolation preprepared solution was added to the fish oil-containing mixture to obtain an oxygen-isolated fish oil-containing solution.

Comparative Example 5

This comparative example was different from Example 1 in that step (2) of the preparation method of the soft candy in this comparative example was as follows: 2 parts of the gum arabic, 0.5 part of the α-cyclodextrin, 2.5 parts of the starch acetate, and 0.5 part of the sucrose fatty acid ester were thoroughly mixed, 5 parts of 60° C. purified water were added, and a resulting mixture was mixed to obtain an oxygen-isolation preprepared solution.

Comparative Example 6

This comparative example was different from Example 1 in that step (1) of the preparation method of the soft candy in this comparative example was as follows: 10 parts of the fish oil, 0.4 part of the orange fragrance, 0.2 part of the lemon fragrance, 0.1 part of the rosemary extract, and 0.1 part of the vitamin E oil were mixed and stirred at 45° C., and then allowed to stand for 45 min to obtain a fish oil-containing mixture.

Effect Example

1. The soft candies prepared in Examples 1 to 3 and Comparative Examples 1 to 6 each were subjected to long-term stability and accelerated stability tests, and a DHA content was used as an evaluation index. Conditions of the long-term stability test were as follows: temperature: 25±2° C., humidity: 25% to 65% RH, and test time: 18 months. Conditions of the accelerated stability test were as follows: temperature: 40±2° C., humidity: 75±5% RH, and test time: 3 months. Test results were shown in Tables 1 and 2.

TABLE 1

Results of the long-term stability test with a DHA content as an evaluation index

| Group | Month 0 | Month 6 | Month 12 | Month 18 |
|---|---|---|---|---|
| Example 1 | 3.11% | 3.12% | 3.08% | 3.06% |
| Example 2 | 12.52% | 12.45% | 12.38% | 12.41% |
| Example 3 | 3.20% | 3.05% | 3.12% | 3.11% |
| Comparative Example 1 | 3.14% | 3.12% | 3.10% | 3.05% |
| Comparative Example 2 | 3.08% | 3.05% | 2.98% | 2.95% |
| Comparative Example 3 | 3.10% | 3.08% | 2.96% | 2.91% |
| Comparative Example 4 | 3.03% | 3.01% | 2.97% | 2.95% |
| Comparative Example 5 | 2.95% | 2.91% | 2.89% | 2.87% |
| Comparative Example 6 | 3.05% | 2.95% | 2.92% | 2.91% |

TABLE 2

Results of the accelerated stability test with a DHA content as an evaluation index

| Group | Month 0 | After accelerated 1 month | After accelerated 2 months | After accelerated 3 months |
|---|---|---|---|---|
| Example 1 | 3.11% | 3.08% | 3.05% | 3.01% |
| Example 2 | 12.52% | 12.47% | 12.42% | 12.39% |
| Example 3 | 3.20% | 3.22% | 3.09% | 3.16% |
| Comparative Example 1 | 3.14% | 3.10% | 3.07% | 3.02% |
| Comparative Example 2 | 3.08% | 3.05% | 2.99% | 2.89% |
| Comparative Example 3 | 3.10% | 3.06% | 2.96% | 2.93% |
| Comparative Example 4 | 3.03% | 3.05% | 2.95% | 2.95% |
| Comparative Example 5 | 2.95% | 2.96% | 2.85% | 2.89% |
| Comparative Example 6 | 3.05% | 2.96% | 2.97% | 2.85% |

2. The soft candies prepared in Examples 1 to 3 and Comparative Examples 1 to 6 each were subjected to long-term stability and accelerated stability tests, and the sensory evaluation was used as an index. Conditions of the long-term stability test were as follows: temperature: 25±2° C., humidity: 25% to 65% RH, and test time: 18 months. Conditions of the accelerated stability test were as follows: temperature: 40±2° C., humidity: 75±5% RH, and test time: 3 months. Specific rules of the sensory evaluation were as follows: 10 food research and development personnel were selected as evaluators for the sensory evaluation, and the soft candies prepared in Examples 1 to 3 and Comparative Examples 1 to 6 were provided in an unknown order to the evaluators for objective evaluation; and scores of the evaluators for each sample were counted, averaged, and listed in the table below (a score was rounded to an integer). Scoring criteria for the sensory evaluation were shown in Table 3, and results of the sensory evaluation were shown in Tables 4 and 5.

TABLE 3

Scoring criteria for the sensory evaluation

| Sensory characteristics | Scoring criteria |
|---|---|
| A: Smell | No fishy odor: 5 points; slight fishy odor: 4 points; acceptable fishy odor: 3 points; obvious fishy odor: 2 points; and strong fishy odor: 1 point |
| B: Taste | No fishy taste: 5 points; slight fishy taste: 4 points; acceptable fishy taste: 3 points; obvious fishy taste: 2 points; and strong fishy taste: 1 point |

TABLE 4

| Results of the long-term stability test with sensory evaluation as an evaluation index | | | | |
|---|---|---|---|---|
| Group | Month 0 | Month 6 | Month 12 | Month 18 |
| Example 1 | A 5 B 5 | A 5 B 5 | A 4 B 5 | A 4 B 5 |
| Example 2 | A 5 B 5 | A 5 B 4 | A 4 B 4 | A 4 B 4 |
| Example 3 | A 5 B 5 | A 5 B 5 | A 5 B 5 | A 4 B 5 |
| Comparative Example 1 | A 4 B 3 | A 3 B 3 | A 2 B 3 | A 1 B 2 |
| Comparative Example 2 | A 4 B 5 | A 3 B 3 | A 2 B 2 | A 1 B 2 |
| Comparative Example 3 | A 4 B 4 | A 3 B 3 | A 2 B 3 | A 2 B 2 |
| Comparative Example 4 | A 4 B 4 | A 4 B 3 | A 3 B 3 | A 2 B 2 |
| Comparative Example 5 | A 4 B 4 | A 3 B 4 | A 3 B 3 | A 2 B 3 |
| Comparative Example 6 | A 4 B 5 | A 3 B 4 | A 3 B 3 | A 2 B 3 |

TABLE 5

| Results of the accelerated stability test with sensory evaluation as an evaluation index | | | | |
|---|---|---|---|---|
| Group | Month 0 | After accelerated 1 month | After accelerated 2 months | After accelerated 3 months |
| Example 1 | A 5 B 5 | A 4 B 5 | A 4 B 5 | A 4 B 4 |
| Example 2 | A 5 B 5 | A 4 B 4 | A 4 B 4 | A 3 B 4 |
| Example 3 | A 5 B 5 | A 4 B 5 | A 4 B 5 | A 4 B 4 |
| Comparative Example 1 | A 4 B 3 | A 3 B 3 | A 2 B 2 | A 1 B 1 |
| Comparative Example 2 | A 4 B 5 | A 3 B 3 | A 1 B 2 | A 1 B 1 |
| Comparative Example 3 | A 4 B 4 | A 3 B 3 | A 2 B 3 | A 2 B 1 |
| Comparative Example 4 | A 4 B 4 | A 3 B 4 | A 2 B 3 | A 1 B 2 |
| Comparative Example 5 | A 4 B 4 | A 3 B 3 | A 2 B 3 | A 2 B 2 |
| Comparative Example 6 | A 4 B 5 | A 3 B 4 | A 2 B 3 | A 2 B 1 |

Finally, it should be noted that the above examples are provided merely to describe the technical solutions of the present disclosure, rather than to limit the protection scope of the present disclosure. Although the present disclosure is described in detail with reference to preferred examples, a person of ordinary skill in the art should understand that modifications or equivalent replacements may be made to the technical solutions of the present disclosure without departing from the spirit and scope of the technical solutions of the present disclosure.

The invention claimed is:

1. A preparation method of a soft candy without a fishy taste or odor, comprising the following steps:

(1) preparation of a docosahexaenoic acid (DHA)-containing mixture, comprising mixing and stirring a DHA-containing raw oil, a fragrance, and an antioxidant, and allowing a resulting mixture to stand to obtain the DHA-containing mixture, wherein in step (1), the mixing and stirring is conducted at 10° C. to 35° C.;

(2) preparation of an oxygen-isolation preprepared solution, comprising mixing a polymeric sugar, an emulsifying agent, and water, and subjecting a resulting mixture to dispersion with a shearing device to obtain the oxygen-isolation preprepared solution, wherein in step (2), the dispersion is conducted at 30° C. to 90° C., and a rotational speed of the shearing device is 1,000 rpm to 6,000 rpm;

(3) preparation of an oxygen-isolated DHA-containing solution, comprising adding the oxygen-isolation preprepared solution and the DHA-containing mixture to a dispersion device to allow dispersion, and allowing a resulting system to undergo equilibrium and stabilization to obtain the oxygen-isolated DHA-containing solution, wherein in step (3), the dispersion is conducted for 10 min to 60 min, and the equilibrium and stabilization is conducted for 0.5 h to 3 h;

(4) preparation of a pigment solution and an acid solution;

(5) preparation of a syrup;

(6) preparation of a sugar-containing slurry, comprising mixing the syrup, the oxygen-isolated DHA-containing solution, the acid solution, and the pigment solution to obtain the sugar-containing slurry; and (7) pouring, comprising pouring the sugar-containing slurry into a soft candy mold for shaping to obtain the soft candy without the fishy taste or odor.

2. The preparation method of the soft candy without the fishy taste or odor according to claim 1, wherein the mixing in step (6) is conducted at a temperature of 50° C. to 75° C. or a temperature of 76° C. to 100° C., when the mixing in step (6) is conducted at 50° C. to 75° C., the mixing is conducted for less than 30 min; and when the mixing in step (6) is conducted at 76° C. to 100° C., the mixing is conducted for less than 20 min.

3. The preparation method of the soft candy without the fishy taste or odor according to claim 1, wherein the pouring for shaping in step (7) is conducted at a temperature of 50° C. to 75° C. or a temperature of 76° C. to 100° C., when the sugar-containing slurry in step (7) has a temperature of 50° C. to 75° C., the pouring for shaping is conducted for less than 2 h; and when the sugar-containing slurry in step (7) has a temperature of 76° C. to 100° C., the pouring for shaping is conducted for less than 1 h.

4. The preparation method of the soft candy without the fishy taste or odor according to claim 1, wherein based on a mass of the DHA-containing raw oil, a mass percentage of the polymeric sugar is 30% to 80%, a mass percentage of the emulsifying agent is 0.1% to 30%, a mass percentage of the fragrance is 0.1% to 50%, and a mass percentage of the antioxidant is 0.1% to 5%.

5. The preparation method of the soft candy without the fishy taste or odor according to claim 2, wherein based on a mass of the DHA-containing raw oil, a mass percentage of the polymeric sugar is 30% to 80%, a mass percentage of the emulsifying agent is 0.1% to 30%, a mass percentage of the fragrance is 0.1% to 50%, and a mass percentage of the antioxidant is 0.1% to 5%.

6. The preparation method of the soft candy without the fishy taste or odor according to claim 3, wherein based on a mass of the DHA-containing raw oil, a mass percentage of the polymeric sugar is 30% to 80%, a mass percentage of the emulsifying agent is 0.1% to 30%, a mass percentage of the fragrance is 0.1% to 50%, and a mass percentage of the antioxidant is 0.1% to 5%.

7. The preparation method of the soft candy without the fishy taste or odor according to claim 1, involving at least one selected from the group consisting of the following (a) to (f):

(a) the fragrance is selected from the group consisting of a citrus fragrance, a berry fragrance, and a mixture thereof;

(b) the antioxidant is selected from the group consisting of a rosemary extract, vitamin E, vitamin C, a tea polyphenol, a phospholipid, and a mixture thereof;

(c) the polymeric sugar is selected from the group consisting of gum arabic, fructo-oligosaccharide (FOS), α-cyclodextrin, β-cyclodextrin, γ-cyclodextrin, maltodextrin, polydextrose, inulin, pectin, carrageenan, guar gum, starch acetate, acetylated distarch, and a mixture thereof;

(d) the emulsifying agent is selected from the group consisting of mono- and diglycerides of fatty acid, sucrose fatty acid esters, phospholipids, citric and fatty acid esters of glycerol, acetylated mono- and diglycerides of fatty acid, sodium caseinate, lactic and fatty acid esters of glycerol, and a mixture thereof;

(e) a sugar used in preparation of the sticky-syrup is selected from the group consisting of maltitol, isomaltitol, glucose, white granulated sugar, and a mixture thereof; and (f) the DHA-containing raw oil is selected from the group consisting of fish oil, algal oil, and a mixture thereof.

8. The preparation method of the soft candy without the fishy taste or odor according to claim 2, involving at least one selected from the group consisting of the following (a) to (f):

(a) the fragrance is selected from the group consisting of a citrus fragrance, a berry fragrance, and a mixture thereof;

(b) the antioxidant is selected from the group consisting of a rosemary extract, vitamin E, vitamin C, a tea polyphenol, a phospholipid, and a mixture thereof;

(c) the polymeric sugar is selected from the group consisting of gum arabic, fructo-oligosaccharide (FOS), α-cyclodextrin, β-cyclodextrin, γ-cyclodextrin, maltodextrin, polydextrose, inulin, pectin, carrageenan, guar gum, starch acetate, acetylated distarch, and a mixture thereof;

(d) the emulsifying agent is selected from the group consisting of mono- and diglycerides of fatty acid, sucrose fatty acid esters, phospholipids, citric and fatty acid esters of glycerol, acetylated mono- and diglycerides of fatty acid, sodium caseinate, lactic and fatty acid esters of glycerol, and a mixture thereof;

(e) a sugar used in preparation of the sticky-syrup is selected from the group consisting of maltitol, isomaltitol, glucose, white granulated sugar, and a mixture thereof; and (f) the DHA-containing raw oil is selected from the group consisting of fish oil, algal oil, and a mixture thereof.

9. The preparation method of the soft candy without the fishy taste or odor according to claim 3, involving at least one selected from the group consisting of the following (a) to (f):

(a) the fragrance is selected from the group consisting of a citrus fragrance, a berry fragrance, and a mixture thereof;

(b) the antioxidant is selected from the group consisting of a rosemary extract, vitamin E, vitamin C, a tea polyphenol, a phospholipid, and a mixture thereof;

(c) the polymeric sugar is selected from the group consisting of gum arabic, fructo-oligosaccharide (FOS), α-cyclodextrin, β-cyclodextrin, γ-cyclodextrin, maltodextrin, polydextrose, inulin, pectin, carrageenan, guar gum, starch acetate, acetylated distarch, and a mixture thereof;

(d) the emulsifying agent is selected from the group consisting of mono- and diglycerides of fatty acid, sucrose fatty acid esters, phospholipids, citric and fatty acid esters of glycerol, acetylated mono- and diglycerides of fatty acid, sodium caseinate, lactic and fatty acid esters of glycerol, and a mixture thereof;

(e) a sugar used in preparation of the syrup is selected from the group consisting of maltitol, isomaltitol, glucose, white granulated sugar, and a mixture thereof; and (f) the DHA-containing raw oil is selected from the group consisting of fish oil, algal oil, and a mixture thereof.

10. The preparation method of the soft candy without the fishy taste or odor according to claim 1, wherein the soft candy without the fishy taste or odor is at least one selected from the group consisting of an animal glue-based soft candy, a plant gum-based soft candy, a mixed glue-based soft candy, a filled soft candy, a coated soft candy, and a double-layer soft candy.

* * * * *